US007295302B2

(12) United States Patent
Magniez (10) Patent No.: US 7,295,302 B2
(45) Date of Patent: Nov. 13, 2007

(54) USE OF LASER REFLECTION PICKUP UNIT FOR DETECTION OF SMALL PARTICLES ON A RELATIVELY SMOOTH AND REFLECTIVE SURFACE

(75) Inventor: Clement A. A. Magniez, Eindhoven (FR)

(73) Assignee: Xerox Corporation, Stamford, CT (US)

( * ) Notice: Subject to any disclaimer, the term of this patent is extended or adjusted under 35 U.S.C. 154(b) by 229 days.

(21) Appl. No.: 10/975,148

(22) Filed: Oct. 28, 2004

(65) Prior Publication Data

US 2006/0092409 A1 May 4, 2006

(51) Int. Cl.
*G01N 21/00* (2006.01)
*G01B 9/02* (2006.01)
*G01B 11/02* (2006.01)
*G01N 21/55* (2006.01)
*G11B 3/00* (2006.01)

(52) U.S. Cl. .................. 356/237.3; 356/484; 356/511; 356/445; 369/99

(58) Field of Classification Search ............... 356/511, 356/484, 445; 369/99
See application file for complete search history.

(56) References Cited

U.S. PATENT DOCUMENTS

| 5,351,229 A | * | 9/1994 | Brezoczky et al. ........... 369/99 |
| 5,519,497 A | * | 5/1996 | Hubble et al. ............... 356/445 |
| 5,687,297 A | | 11/1997 | Coonan et al. |
| 5,875,029 A | * | 2/1999 | Jann et al. ................... 356/511 |
| 5,883,714 A | * | 3/1999 | Jann et al. ................... 356/484 |
| 6,069,624 A | | 5/2000 | Dash et al. |

* cited by examiner

*Primary Examiner*—Gregory J. Toatley, Jr.
*Assistant Examiner*—Iyabo S Alli
(74) *Attorney, Agent, or Firm*—Oliff & Berridge, PLC (57) ABSTRACT

A method and apparatus for detecting stray particles upon a relatively smooth surface by measuring the amount of collimated light reflected from the surface from clear areas of the surface and from particles resting on the surface. Optical pick-up units similar to those used in DVD's and CD's can be used. A method for detecting defective depressions is also covered.

35 Claims, 5 Drawing Sheets

USE OF LASER REFLECTION PICKUP UNIT FOR DETECTION OF SMALL PARTICLES ON A RELATIVELY SMOOTH AND REFLECTIVE SURFACE

BACKGROUND AND SUMMARY

The present invention applies generally to the use of optical reflection pickup units to detect randomly placed small or microscopic particles on a relatively smooth and reflective surface. One embodiment of the invention is the use of an optical pickup unit to detect toner particles on an electrophotographic imaging surface that have escaped removal during the surface cleaning process.

Many manufacturing and imaging processes require periodic removal of dust and other microscopic particles from relatively smooth surfaces. Examples include, without limitation, cleaning of vessels, tubes, molds, forms, and other holding, processing, shaping, and transferring equipment used in clean-room environments and in other environments where removal of stray particles is important for imaging, purification, or contamination purposes. Often, a primary cleaning process is used, and, depending upon its efficacy, sufficient cleaning may be assumed. Where the primary cleaning process is not dependable for such assurance, where the cleaning system is understood to degrade over time, or where no cleaning system is used, it would be useful to employ an accurate and repeatable system for detecting and measuring stray particles that remain on relatively smooth surfaces of the equipment that is desired to be clean before or during the next use.

One such situation described in the preceding paragraph occurs in electrostatographic imaging systems such as electrophotographic printers. Modern toners range in size from about 4 microns to about 20 microns. After toner is imaged on a drum, belt, or other charged imaging surface, such toner is transferred to a copy sheet. Transfer of such toner is known not to be complete. A primary cleaning system is accordingly employed post-imaging in order to prepare the imaging surface for recharging and reuse. Primary cleaning systems known in the art generally comprise either brushes or blades or combinations of both. Such cleaning systems are known to degrade over time, requiring periodic replacement. Even without cleaning degradation, some stray particles often escape the cleaning system.

When designing the projected maintenance schedule of a new printer, thousands of images are typically run in order to develop a statistical understanding of the rate at which primary cleaning systems degrade and to predict the time at which preventive maintenance should occur. Current methods for detecting degradation of the cleaning system generally comprise either close human inspection of copy sheets or the imaging surface to detect unacceptable levels of stray toner and debris that escaped cleaning or inspection of the amount of post-cleaning stray toner and debris that is removed from the imaging surface by tape, cleaning fluids, vacuums, or properly charged rollers. Both methods of inspection (inspection of stray toner and debris on surfaces or inspection of stray toner and debris after removal) are inaccurate and non-reproducible due to the inability of humans to quantitatively measure small and randomly placed quantities. Nevertheless, with much testing and inspection, a degradation profile is statistically generated for the applicable cleaning system. Because of wide statistical deviations in determinations of unacceptable cleaning results, the final maintenance schedule tends to call for replacement or repair of cleaning elements somewhat earlier than would be the case with better measurements resulting in smaller statistical deviations in the cleaning measurement results.

Once a printer is launched and in normal use, maintenance personnel and operators monitor cleaning efficacy using the same techniques described above. Because measurement of toner and debris left on copy or imaging surfaces or removed by tape or other removal techniques is inherently inaccurate and non-reproducible, those monitoring cleaning efficacy often actually replace cleaning elements too often or too infrequently, resulting either in higher maintenance costs or unnecessarily poor image quality.

It would be desirable to invent an accurate and reproducible stray particle detection system that produces measurable and predictive results. It is also desirable that such a system be able to detect even single particles ranging from about 1 micron to a few tens of microns in size, even if not visually detectable with human eyes.

One embodiment of the invention is a method for detecting one or more particles on a surface, such surface having areas clear of particles and such particles having a profile, such method comprising: focusing collimated light upon a clear area of the surface; measuring, with a sensor, the strength of signal reflected from the clear area of the surface; traversing the focused collimated light over the surface until it illuminates a particle; measuring, with a sensor, the strength of signal reflected from the particle; comparing with the strength of signal reflected from a clear area with the strength of signal reflected from the particle; and determining the existence of the particle by the comparison of the signals from the clear area and the particle.

Another embodiment of the invention is a method for detecting one or more depression defects on a surface, such surface having areas clear of particles and such depression defects having a profile, such method comprising: focusing collimated light upon a clear area of the surface; measuring, with a sensor, the strength of signal reflected from the clear area of the surface; traversing the focused collimated light over the surface until it illuminates a depression defect; measuring, with a sensor, the strength of signal reflected from the depression defect; comparing with the strength of signal reflected from a clear area with the strength of signal reflected from the depression defect; and determining the existence of the depression defect by the comparison of the signals from the clear area and the depression defect.

Yet another embodiment of the invention is a device for detecting particles on a surface, such surface having areas clear of particles, and such device comprising: a plurality of collimated light sources wherein the light from each is focused on a spot on the surface; a plurality of sensors, each coupled with a light source, for detecting light reflected from the surface from the coupled light source; wherein more light from a light source is reflected to the coupled sensor from clear areas of the surface than from particles.

DETAILED DESCRIPTION

For a general understanding of the present invention, reference is made to the drawings. In the drawings, like reference numerals have been used throughout to designate identical elements.

As described above, embodiments of the present invention have a wide number of possible applications, including without limitation, in the imaging industry and in industries such as optical quality glass manufacturing, pharmaceuticals, semi-conductors, and other industries where detection of microscopic or near-microscopic particles on relatively smooth surfaces is desired. An embodiment useful in electrophotographic printers is described as one example of possible embodiments and applications.

An exemplary electronic system comprising one embodiment of the present invention is a multifunctional printer with print, copy, scan, and fax services. Such multifunctional printers are well known in the art and may comprise print engines based upon ink jet, electrophotography, and other imaging devices. The general principles of electrophotographic imaging are well known to many skilled in the art. Generally, the process of electrophotographic reproduction is initiated by substantially uniformly charging a photoreceptive member, followed by exposing a light image of an original document thereon. Exposing the charged photoreceptive member to a light image discharges a photoconductive surface layer in areas corresponding to non-image areas in the original document, while maintaining the charge on image areas for creating an electrostatic latent image of the original document on the photoreceptive member. This latent image is subsequently developed into a visible image by a process in which a charged developing material is deposited onto the photoconductive surface layer, such that the developing material is attracted to the charged image areas on the photoreceptive member. Thereafter, the developing material is transferred from the photoreceptive member to a copy sheet or some other image support substrate to which the image may be permanently affixed for producing a reproduction of the original document. In a final step in the process, the photoconductive surface layer of the photoreceptive member is cleaned to remove any residual developing material therefrom, in preparation for successive imaging cycles.

The above described electrophotographic reproduction process is well known and is useful for both digital copying and printing as well as for light lens copying from an original. In many of these applications, the process described above operates to form a latent image on an imaging member by discharge of the charge in locations in which photons from a lens, laser, or LED strike the photoreceptor. Such printing processes typically develop toner on the discharged area, known as DAD, or "write black" systems. Light lens generated image systems typically develop toner on the charged areas, known as CAD, or "write white" systems. Embodiments of the present invention apply to both DAD and CAD systems. Since electrophotographic imaging technology is so well known, further description is not necessary. See, for reference, e.g., U.S. Pat. No. 6,069,624 issued to Dash, et al. and U.S. Pat. No. 5,687,297 issued to Coonan et al., both of which are hereby incorporated herein by reference.

Figure 1:
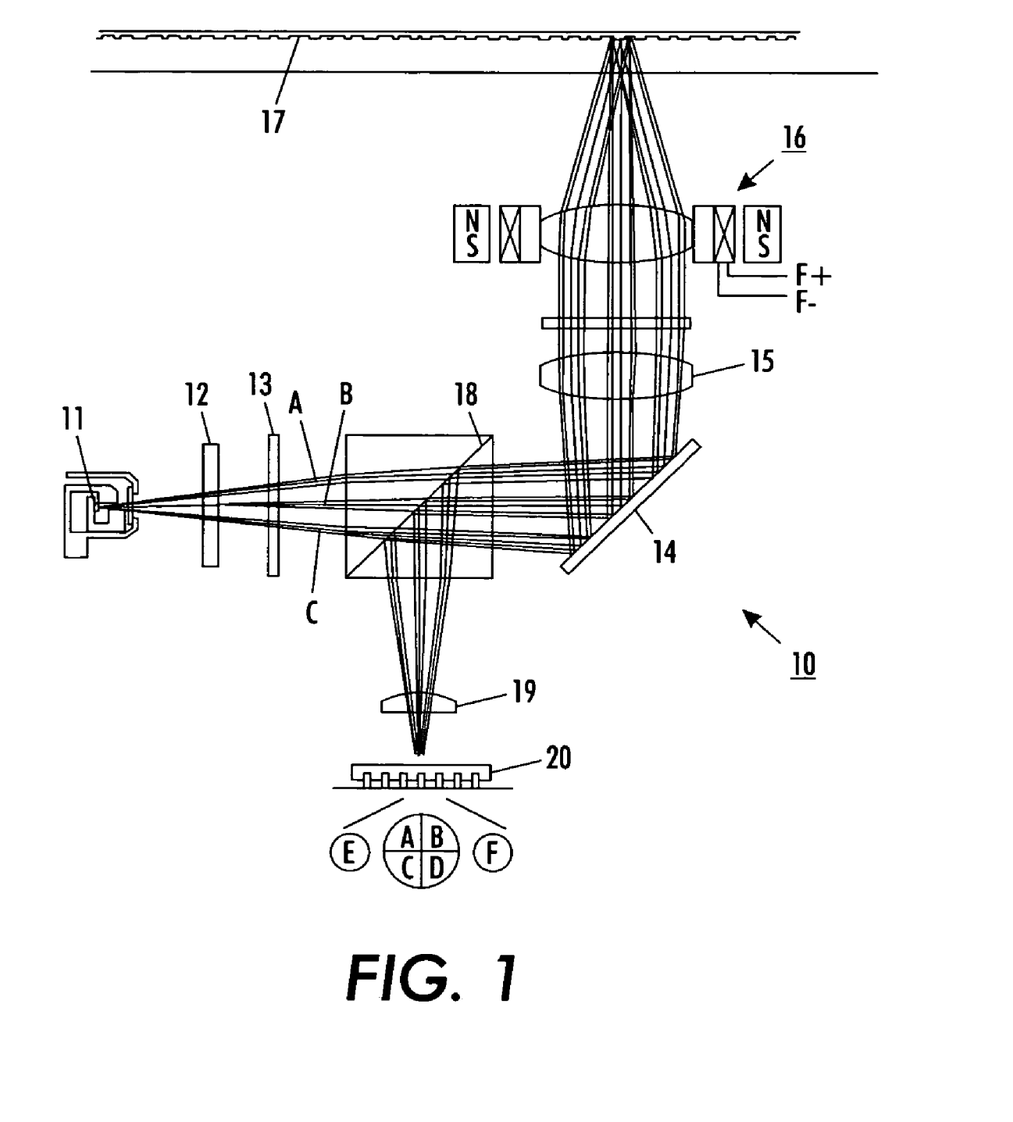
FIG. 1 is an exploded schematic view of an Optical Pick-Up unit of the prior art usable with the present invention.

Referring to FIG. 1, a schematic view of one embodiment of the detector system of the present invention is shown. This embodiment employs a typical optical pickup unit (OPU) usable for DVD's, CD's, optical disks, and similar applications. Optical pickup units are made by Philips Corporation based in Netherlands, SONY and Sanyo based in Japan, and numerous other manufacturers and suppliers to the audio and entertainment industry. Such devices are well known in the art, and only a summary description is provided herein. When used in a typical DVD or CD player, such devices detect areas of strong reflected signals interspersed with optically dark spots or actual "pits" that reflect measurably less signal back to the detector.

In FIG. 1, OPU unit 10 is mounted on a movable carriage (not shown) or other mounting device that allows it to transverse a surface to be measured. OPU unit 10 contains a laser diode unit 11 that produces a laser beam emitted as 3 beams from the unit. Such laser beam in a typical CD OPU has a wavelength of 790+10, −15 nanometers, while a blue laser used for DVD OPU units typically has a 655+5, −10 nanometer wavelength. Outboard beams A and C are used primarily for tracking the OPU unit's travel across the surface being measured. A diffraction grating 12 further splits and gives direction to each beam, and polarizer screen 13 ensures that each beam is polarized. Each beam hits a turning mirror 14, which reflects the beams toward collimating lens 15. Focus unit 16 controls focus of the beam with electromagnets used to adjust an objective lens. As will be explained below, focus is actively managed using readouts from beams A, B, and C. The depth of focus of an OPU unit such as OPU unit 10 for a CD OPU unit is typically around 1.9 micrometer. For a blue DVD OPU unit, the depth of focus is typically around 0.85 micrometer. Upon being focused upon surface 17, beams A, B, and C are reflected back through focus unit 16, which acts as a collimating lens. Collimating lens 15, in turn, acts as an objective lens to begin focusing the beams to a single point. The beams are then reflected by a polarizing beam splitter 18 toward a cylindrical lens 19, which provides final focus upon a photodiode array readout unit 20.

Generally, main beam B focused at the center of photodiode array 20 and is used for data readout and focus. When the beam is focused on a clean area of surface 17, the readout from photodiode detector 20 indicates a measurably stronger signal than when the unit is out of focus. Since most of the surface is smooth, moving the carriage containing OPU unit 10 over a short distance while varying the degree of focus quickly calibrates an optimal depth of field to be used when scanning a smooth surface mounted orthogonally to beams A, B, and C. The readout from beam B is maximized at an optimal depth of field, and any major drop in signal during traverse of OPU 10 indicates either that focus has been lost or that beam B has been scattered or unfocused by something on or in surface 17. Depending upon the application, recurring focus calibration may be required during carriage traverse in order to maintain a strong average signal detected by photodiode array 20. Beams A and C, while vital for tracking on a DVD or CD, are not necessary for some embodiments of the present invention but may be important where tracking of the OPU unit is utilized during the application. In other embodiments of the invention, beams A and C may be used to compute and control the velocity of the carriage carrying the OPU unit. Carriage velocity can be measured by measuring the time between detection of a stray particle by either beams A or C and detection of the same particle by beam B. Beams A and C can also be used to corroborate data received from main beam B.

Figure 2:
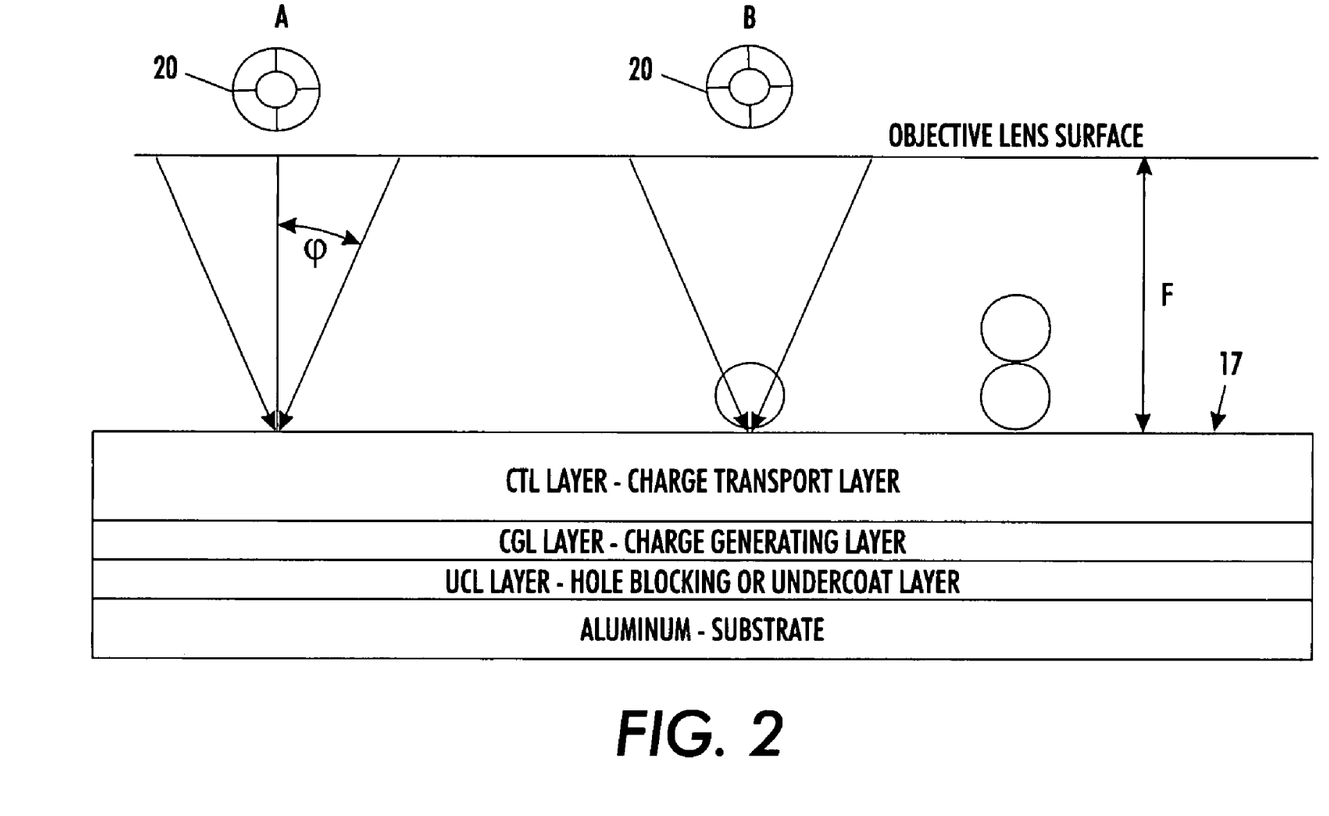
FIG. 2 is a plan schematic view of an embodiment of the present invention scanning the surface of a photoconductive imaging media.

Referring to FIG. 2, a simplified schematic plan view shows how OPU unit 10 works to detect stray particles such as toner particles. In FIG. 2, photodiode detector array 20 is shown in both scenario A and scenario B. The focal length between adjustable objective lens 16 and imaging surface 17 is indicated by letter F. For a typical CD OPU unit, F is about 2.98 millimeters. Surface 17 comprises the top surface of one of 4 layers of a photoconductive drum, endless loop, or other photoconductive media. The top layer, labeled CTL, comprises the Charge Transport Layer of the photoconductive media, which transports a charge to the imaging surface. The adjoining layer, labeled CGL, is the Charge Generating Layer, which generates a charge in response to light. The next layer is labeled UCL, for UnderCoat Layer, which insulates the CGL and CTL layers from the underlying substrate. The substrate layer is labeled aluminum, which is a standard substrate for drums and many endless loop photoconductors. The listed layers and additional layers typically found in photoconductive imaging media contain are well known in the art, and further explanation for purposes of the present invention is not required.

In scenario A of FIG. 2, beam B has been emitted by laser diode 11 (Shown in FIG. 1) and is focused upon surface 17. Because nothing obscures or blocks its reflection, beam B reflects off surface 17 and back through the optics shown in FIG. 1 and onto photodiode detector array 20. Some scattering of the beam occurs upon reflection but is generally contained within angle $\phi$. The intensity of light received at photodiode detector array 20 exceeds its null threshold, and a positive reflection signal is indicated in FIG. 2 by the open circle in the middle of photodiode array 20. (If surface 17 were the surface of a DVD, scenario A would signify that no bit was found at the focused point of beam B.) In contrast, scenario B shows the effect that a particle such as a toner particle has upon the intensity of reflected beam B. In scenario B, a particle rests on surface 17. When beam B strikes, it is scattered or absorbed by the particle. Photodiode detector 20 receives little or no return signal, and its null threshold is not exceeded. The darkened center of photodiode detector 20 signifies that an insufficient return signal has been received. For purposes of this application, "particle" means any foreign material or defects on the surface being measured. "Particles" include, without limitation, debris, actual particles, fibers, smears, surface clumps, ridges, and similar raised features that absorb or scatter light and that are not desired to be on the measured surface. Embodiments of the present invention may also be used to detect scratches, gouges, pits, valleys, or other depressed features that absorb or scatter light and that are not desired to be on the measured surface.

Figure 3:
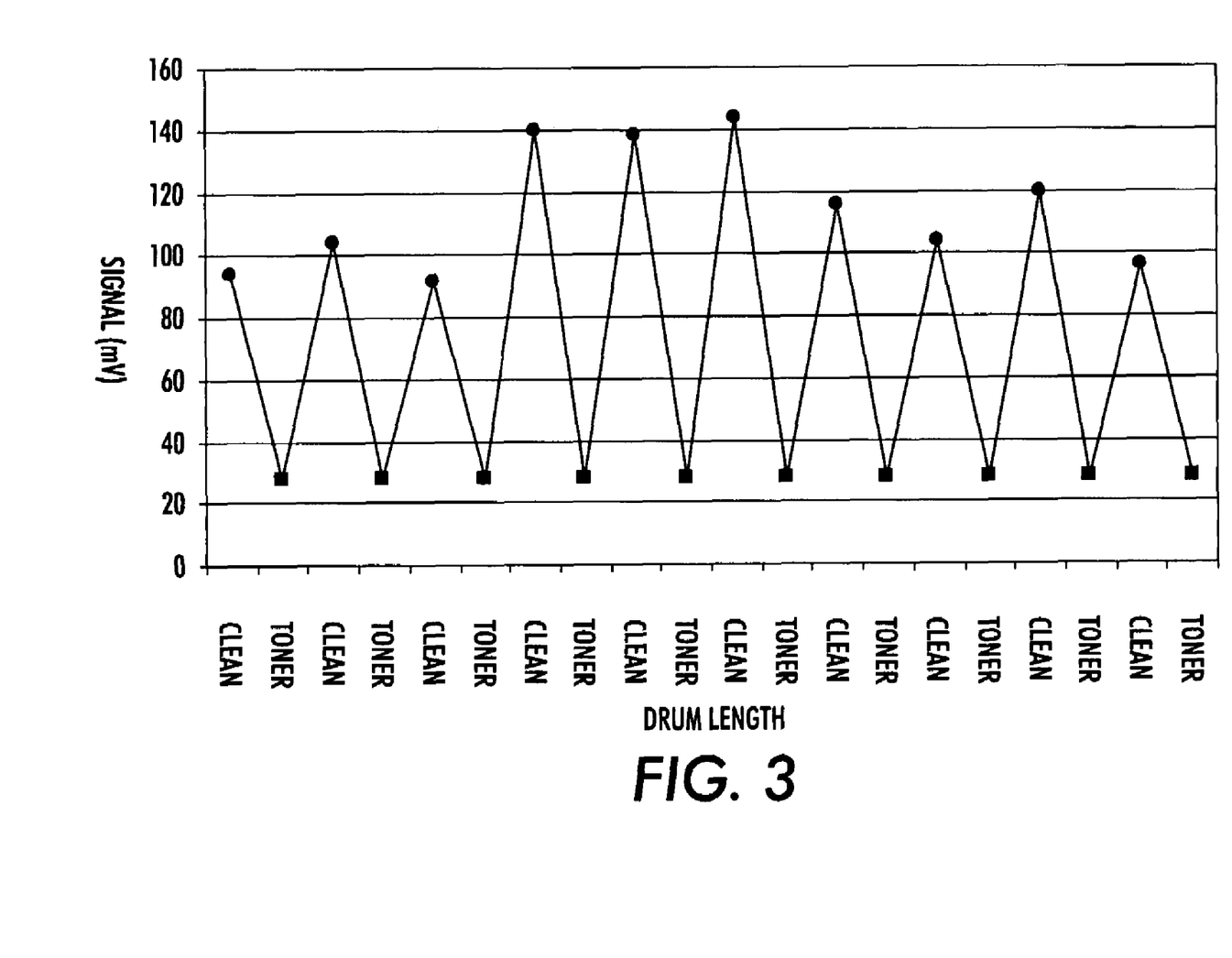
FIG. 3 is a graph showing exemplary photodiode sensor array readouts from clean and toner covered areas of the surface of a photoconductive imaging medium.

FIG. 3 is a graph showing readouts from photodiode detector 20 as its carriage traverses the width of a photoconductor (a drum) that contains small streaks of toner spaced along an otherwise clean surface. As expected, strong signals are received whenever photodiode detector 20 passes over clean areas while weak signals are received whenever toner streaks are encountered. The signals from clean areas generally exceed 5 times the strength of signals from areas having toner. This large signal difference corroborates the reliability of the detector and its ability to accurately discriminate between clean and surfaces covered with particles. In order to produce such a clear signal, it is best if the particles to be detected are expected to have a profile across the illuminating light that is large enough to absorb or scatter a significant amount of the light signal. Where, as shown in FIG. 3, the difference between clear and obstructed signal is approximately a factor of 5, it is believed that an adequate signal can be detected and measured if the profile of the particle obscures at least about thirty (30) percent of the illuminated spot. Stated inversely, measurable detection of particles is possible as long as the focused spot of light is not more than about three (3) times the profile of the particle to be detected.

Tests confirm that the optics and laser of an OPU unit designed for a CD or DVD can detect single particles varying in size from about 4 microns to about 20 microns, which is the size of typical modern toner particles. Larger particles are also obviously detectable. For a 20 micron toner particle, a spot size of about 60 microns or less can be used. For a 4 micron toner particle, a spot size of about 12 microns or less can be used. Smaller spot sizes can resolve smaller particles and can also be used to detect particles much larger than the spot. While spots created by OPU units are generally essentially circular, elliptical or irregularly shaped spots are also usable with the present invention. The most relevant dimension of such non-circular spots is the distance across, or orthogonal, to the scanning axis, i.e., orthogonal to the direction in which the media is being scanned. With a standard CD OPU units using a 790 nanometer wavelength, a spot as small as about 0.86 micrometers can be resolved. With a blue DVD OPU unit having a 655 nanometer wavelength, spot sizes as small as 0.5 micrometers can be resolved. A formula for estimating the resolution of a resolvable spot of toner or debris on a surface is the following: $d=(2M^2\lambda)/\pi NA = \lambda/2NA$, where d is the resolvable spot size, $\lambda$ is the applicable wavelength, and NA is the numerical aperture value of the optics system. Depth of focus for such a system is given by the following formula: Depth of Focus=d/NA.

As discussed above, resolution of the spot size using a laser is a function of wavelength and optics. The invention does not require a laser, however. Any source of collimated light would suffice with properly designed sensors (such as photodiode array sensor 20 in FIG. 1). A non-laser light source would presumably emit multiple wavelengths. A preference would be a light source that emits monochromatic or nearly monochromatic light in order to simplify optics and sensor apparatus. With proper focus and sufficient light intensity, such multi-wavelength systems would perform adequately.

The smoother and more reflective surface 17 may be, the more sensitive the detection ability of the present invention. Tests to date have been successfully conducted on surfaces with roughness measurements of Ra ranging from about 0.01 to about 0.25 micrometers and Rymax from about 0.20 to about 2 micrometers. Ra is a measure of the average roughness centerline of irregularities on a surface, and Rymax is a measure of the maximum peak to valley height of such irregularities. Other tests confirm that when a carriage holding an OPU unit is moved across a photoconductor surface, an out-of-focus status can be detected and differentiated from the presence of particles. Similarly, tests confirm that the system is capable of focusing upon top surface 17 without confusion being introduced by multilayer substrates similar to the one shown in FIG. 2. Lastly, tests confirm that results are repeatable between different surfaces having the same general smoothness and reflectance properties.

The reflectance of the surface to be measured (e.g., surface 17 of FIG. 1) is also a factor affecting the effectiveness of the present invention. Reflectance is the irradiance ratio between the reflecting beam and the incident beam. A formula for reflectance is as follows: $R=[(n_1-n_2)/(n_1+n_2)]^2$, where $n_1$ is the index of refraction of air (the transmitting medium) and $n_2$ is the index of refraction of the material upon the surface being reflected. The average surface of CD's and DVD's are highly reflective. Standard OPU units accordingly output low intensity light beams of using lasers emitting approximately 0.5 milliWatts of power. In experiments using standard photoreceptors for surface 17, such low power light emissions have proven adequate to produce reliable return signals. The index of refraction of tested photoreceptor surfaces has ranged from about 1.4 to about 1.7. Materials having index of refractions greater than about 1.4 can accordingly be deemed suitable for use with embodiments of the present invention using standard 5 mW lasers of standard OPU units on the market at the present time. For surfaces comprised of materials having lower indices of refraction, embodiments of the present invention may work satisfactorily or more light intensity may be required.

Figure 4:
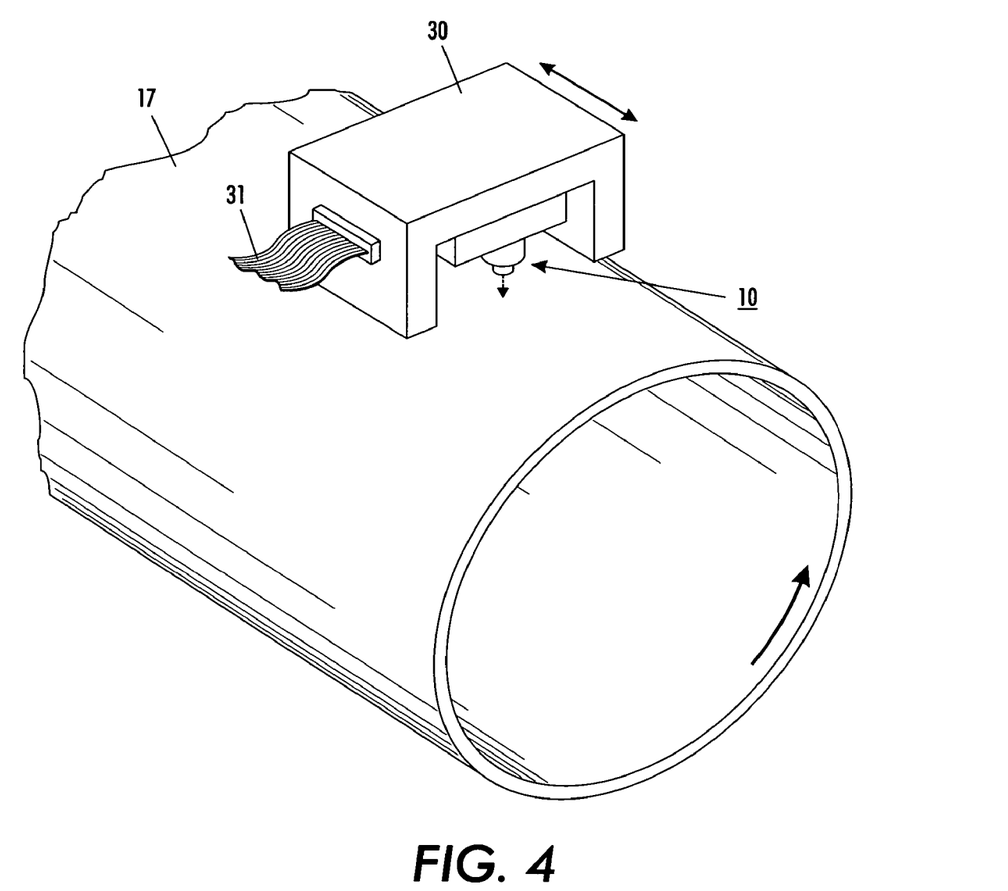
FIG. 4 is an elevated perspective view of an embodiment of the present invention in which an Optical Pick-Up unit is mounted on a carriage traversing a photoconductive drum.

Referring to FIG. 4, a simple embodiment of a single OPU unit mounted on a traversing carriage 30 is shown. In this elevated perspective view, carriage 30 holds OPU unit 10 above photoconductive drum surface 17. Readout ribbon cable 31 is shown to the left. A mechanism to steer and drive carriage 30 is not shown but is easily constructed by those skilled in the art. Traverse speeds may vary by application but may be fairly high. For instance, the effective OPU-to-DVD speed at the outside of a DVD is known to be about 1.2 meters/second.

Figure 5:
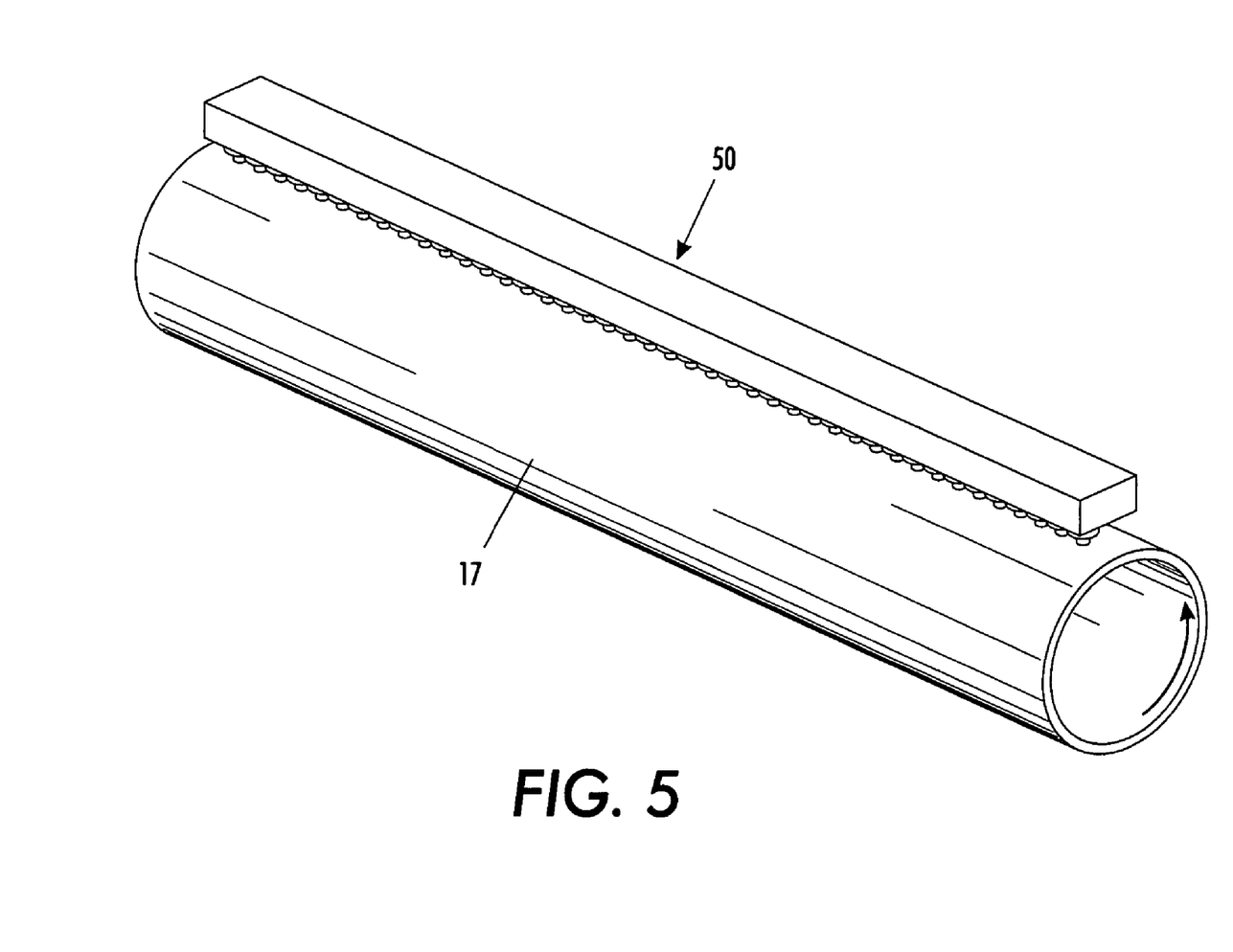
FIG. 5 is an elevated perspective view of a linear array embodiment of the present invention

One embodiment if a full-width particle detector need not use fast traverse speeds. Instead, a drum or endless loop can be made to rotate underneath carriage 30 as shown in FIG. 4. With each revolution, carriage 30 advances the width of one detection path, or approximately 1 micrometer, which is in the range of about 1 to about 2 times the amount of distance across the spot. OPU unit 10 then measures particles on the next revolution. The carriage next advances another detection width, and so forth. Yet another embodiment of the present invention that permits more rapid coverage is to use multiple OPU units 10 arranged in an array. Using wide-width array technology widely used in imaging technology for scanners and writers, and printheads, OPU units can be fabricated into arrays of desired lengths that cover all or multiple portions of a surface to be inspected. In a linear array formation, any spaces between discrete OPU units can be covered by traversing the space between OPU units. For instance, if 8 individual OPU units are evenly spaced along a bar 50, as shown in FIG. 5. and if a 9 inch wide surface is to be inspected, then each OPU unit need only traverse one inch in order for the entire width of the surface to be measured. The greater the number of OPU units and the closer their spacing, the less traversing need occur. A full-width array of OPU units would eliminate any need for traverse motion. Yet other embodiments may take the form of area arrays capable of scanning whole areas of a surface simultaneously with or without being mounted on a movable carriage or other means of moving the surface in relation to the array. In other embodiments, the traverse path of an OPU unit may form a helical path across rotating surface such as the surface of a drum or endless loop.

In sum, embodiments of the present invention have been described that enable accurate and reproducible measures of particle contamination on relatively smooth surfaces. This ability to automatically measure even a single particle is a great advance over current methods requiring human inspection of image defects, particles captured by tape or vacuum, or other current methods of detecting particles too small to be easily noticed by normal human vision. Applications of the present invention have been explained in relation to detection of electostatographic particles, both during initial equipment design and during operation in the field. Many other applications are possible, including in industries such as pharmaceuticals, optic quality glass manufacture (including fiber optics), semi-conductors, and any application where non-destructive detection of stray particles is important.

While particular embodiments have been described, alternatives, modifications, variations, and substantial equivalents that are or may be presently unforeseen may arise to applicants or others skilled in the art. Accordingly, the appended claims as filed and as they may be amended are intended to embrace all such alternatives, modifications, variations, improvements, and substantial equivalents The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others.

What is claimed is:

1. A method for detecting one or more particles on a surface, such surface having areas clear of particles and such particles having a profile, such method comprising:
    focusing collimated light upon a clear area of the surface;
    measuring, with a sensor, the strength of signal reflected from the clear area of the surface;
    traversing the focused collimated light over the surface until it illuminates a particle;
    measuring, with a sensor, the strength of signal reflected from the particle;
    comparing the strength of signal reflected from a clear area with the strength of signal reflected from the particle; and
    determining the existence of the particles by the comparison of the signals from the clear area and the particle,
    wherein focusing collimated light comprises focusing a plurality of beams of collimated light upon the surface wherein at least one beam is used to track the traversing over the surface.

2. The method of claim 1, wherein the collimated light comprises light from a laser light source.

3. The method of claim 1, wherein focusing further comprises focusing light on a spot with an area less than 3 times the profile of particles desired to be detected.

4. The method of claim 1, wherein focusing further comprises focusing light on a spot less than 60 microns across.

5. The method of claim 1, wherein focusing further comprises focusing on a spot less than 20 microns across.

6. The method of claim 1, wherein focusing further comprises focusing on a spot less than 10 microns across.

7. The method of claim 1, wherein focusing further comprises focusing on a spot approximately 0.86 micrometers across.

8. The method of claim 1, wherein focusing further comprises focusing upon a spot approximately 0.5 micrometers across.

9. The method of claim 1, wherein the surface is the surface of an electrostatographic imaging surface.

10. The method of claim 1, wherein the surface is the surface of a photoconductive media.

11. The method of claim 1, further comprising arranging a plurality of light sources and sensors in a linear array.

12. The method of claim 1, further comprising arranging a plurality of light sources and sensors in an area array.

13. The method of claim 1, wherein traversing comprises holding the collimated light stationary and moving the surface in relation to the light.

14. The method of claim 13, wherein the collimated light is focused into a spot on the surface and wherein traversing further comprises intermittently moving the spot the distance of from about 1 to about 2 times the amount of distance across the spot.

15. The method of claim 1, wherein traversing comprises moving the collimated light and the surface in a helical relationship to each other.

16. The method of claim 1, wherein traversing comprises moving the light in relation to the surface at a rate of about 1.2 meters per second.

17. A method for detecting one or more particles on a surface, such surface having areas clear of particles and such particles having a profile, such method comprising:
  focusing collimated light upon a clear area of the surface;
  measuring, with a sensor, the strength of signal reflected from the clear area of the surface;
  traversing the focused collimated light over the surface until it illuminates a particle;
  measuring, with a sensor, the strength of signal reflected from the particle;
  comparing the strength of signal reflected from a clear area with the strength of signal reflected from the particle; and
  determining the existence of the particles by the comparison of the signals from the clear area and the particle,
  wherein the surface has an index of refraction exceeding about 1.4.

18. A method for detecting one or more particles on a surface, such surface having areas clear of particles and such particles having a profile, such method comprising:
  focusing collimated light upon a clear area of the surface;
  measuring, with a sensor, the strength of signal reflected from the clear area of the surface;
  traversing the focused collimated light over the surface until it illuminates a particle;
  measuring, with a sensor, the strength of signal reflected from the particle;
  comparing the strength of signal reflected from a clear area with the strength of signal reflected from the particle; and
  determining the existence of the particles by the comparison of the signals from the clear area and the particle,
  wherein the collimated light comprises an energy equal to or greater than about 0.5 milliWatts.

19. The method of claim 1, wherein the surface has a roughness measurement ranging from about 0.01 to about 0.25 micrometers.

20. The method of claim 1, wherein the collimated light comprises light with a wavelength ranging from about 655+5, −10 nanometers.

21. The method of claim 1, wherein the collimated light comprises light with a wavelength ranging from about 790+10, −15 nanometers.

22. The method of claim 1, wherein the source of collimated light and the sensor comprise components of a optical pick-up unit usable for DVD's.

23. The method of claim 1, wherein the source of collimated light and the sensor comprise components of a optical pick-up unit usable for CD's.

24. The method of claim 1, wherein the measuring of the strength of signal reflected from the clear area is repeated for calibration purposes.

25. The method of claim 1, wherein the sensor has a null threshold and wherein determining comprises determining whether the signal reflected from an area exceeds the null threshold.

26. The method of claim 1, further comprising focusing a plurality of beams of collimated light upon the surface wherein at least one beam is used to measure the velocity of the traversing over the surface.

27. The method of claim 1, further comprising focusing a plurality of beams of collimated light upon the surface wherein at least one beam is used to corroborate the reflected signal from another of the beams.

28. The method of claim 1, wherein the sensor for measuring the signal reflected from the clear area is the same sensor used for measuring the signal reflected from the particle.

29. The method of claim 1, wherein the sensor for measuring the signal reflected from the clear area is a photodiode array.

30. A method for detecting one or more depression defects on a surface, such surface having areas clear to depression defects and such depression defects having a profile, such method comprising:
  focusing collimated light upon a clear area of the surface;
  measuring, with a sensor, the strength of signal reflected from the clear area of the surface;
  traversing the focused collimated light over the surface until it illuminates a depression defect;
  measuring, with a sensor, the strength of signal reflected from the depression defect;
  comparing the strength of signal reflected from a clear area with the strength of signal reflected from the depression defect; and
  determining the existence of the depression defect by the comparison of the signals from the clear area and the depression defect; and
  wherein traversing comprises moving the light in relation to the surface at a rate of about 1.2 meters per second.

31. A device for detecting particles on a surface, such surface having areas clear of particles, and such device comprising:
  a plurality of collimated light sources wherein the light from each is focused on a spot on the surface, the spot being approximately 0.5 micrometers across;
  a plurality of sensors, each coupled with a light source, for detecting light reflected from the surface from the coupled light source;
  wherein more light from a light source is reflected to the coupled sensor from clear areas of the surface than from particles.

32. The device of claim 31, wherein the particles have a profile and wherein the focused spot of the surface is not more than about three times the profile of particles to be detected.

33. The device of claim 31, wherein the plurality of collimated light sources comprise lasers.

34. The device of claim 31, wherein at least one beam is used to track the traversing over the surface.

35. The device of claim 31, further comprise a controller that moves the light in relation to the surface at a rate of about 1.2 meters per second.

* * * * *